US007749450B2

(12) United States Patent
Ohse et al.

(10) Patent No.: US 7,749,450 B2
(45) **Date of Patent: *Jul. 6, 2010**

(54) FLUID HANDLING APPARATUS AND FLUID HANDLING UNIT FOR USE THEREIN

(75) Inventors: Takuhito Ohse, Saitama (JP); Noriyuki Kawahara, Saitama (JP); Masanobu Natsuhara, Koshigaya (JP)

(73) Assignee: Enplas Corporation, Saitama (JP)

( * ) Notice: Subject to any disclaimer, the term of this patent is extended or adjusted under 35 U.S.C. 154(b) by 774 days.

This patent is subject to a terminal disclaimer.

(21) Appl. No.: 11/599,508

(22) Filed: Nov. 13, 2006

(65) Prior Publication Data

US 2007/0111304 A1 May 17, 2007

(30) Foreign Application Priority Data

Nov. 14, 2005 (JP) ............................ 2005-328427

(51) Int. Cl.

| | |
|---|---|
| ***B01L 99/00*** | (2010.01) |
| ***G01N 33/00*** | (2006.01) |
| ***B01L 3/00*** | (2006.01) |
| ***C12M 1/00*** | (2006.01) |
| ***C12M 3/00*** | (2006.01) |

(52) U.S. Cl. ........................ 422/101; 422/68.1; 422/99; 422/102; 435/287.2; 435/287.9; 435/288.4

(58) Field of Classification Search .................. 422/102
See application file for complete search history.

(56) References Cited

U.S. PATENT DOCUMENTS 4,865,813 A * 9/1989 Leon .......................... 422/101
5,650,125 A * 7/1997 Bosanquet .................. 422/102
7,001,774 B1 * 2/2006 Gamble et al. ................ 436/54
7,556,778 B2 * 7/2009 Kawahara et al. ........... 422/102

(Continued)

FOREIGN PATENT DOCUMENTS

EP 1291074 A1 3/2003

(Continued)

OTHER PUBLICATIONS

European Search Report, Application No. EP 06 02 3463, dated May 26, 2008.

*Primary Examiner*—Jill Warden
*Assistant Examiner*—Charles Hammond
(74) *Attorney, Agent, or Firm*—Buchman & LaPointe, P.C.

(57) ABSTRACT

A fluid handling apparatus 10 has a plurality of fluid handling subassemblies 16, each of which is mounted in a corresponding one of mounting recessed portions 14 of a plate body 12. Each of the fluid handling subassemblies 16 includes: an injecting section 26 for injecting a fluid; a fluidized section 28 for receiving the fluid from the injecting section 26 to allow the fluid to continuously flow downwards; a fluid housing chamber 30 for receiving the fluid from the fluidized section 28; a wall portion 20 formed so as to extend in substantially vertical directions between the fluid housing chamber 30 and the fluidized section 28; an opening **20*a* for allowing the fluid in the fluidized section 28 to enter the fluid housing chamber 30; and a surface-area increasing means (22, 32, 34) for increasing the area of a contact surface with the fluid in the fluidized section 28**.

15 Claims, 8 Drawing Sheets

U.S. PATENT DOCUMENTS

| | | | | |
|---|---|---|---|---|
| 7,662,345 | B2 * | 2/2010 | Kawahara et al. | 422/101 |
| 2002/0106310 | A1 * | 8/2002 | Zuk | 422/102 |
| 2004/0062688 | A1 * | 4/2004 | Guiles et al. | 422/102 |
| 2004/0185576 | A1 | 9/2004 | Bopp | |
| 2005/0136546 | A1 * | 6/2005 | Berndt et al. | 436/45 |

FOREIGN PATENT DOCUMENTS

| | | | |
|---|---|---|---|
| EP | 1547686 | A1 | 6/2005 |
| JP | 9-101302 | | 4/1997 |
| JP | 9-159673 | | 6/1997 |
| JP | 2001-4628 | | 1/2001 |
| WO | WO02103331 | A1 | 12/2002 |
| WO | WO2004/004886 | A2 | 1/2004 |

* cited by examiner

FLUID HANDLING APPARATUS AND FLUID HANDLING UNIT FOR USE THEREIN

BACKGROUND OF THE INVENTION

1. Field of the Invention

The present invention generally relates to a fluid handling apparatus and a fluid handling unit for use therein. More specifically, the invention relates to a fluid handling apparatus capable of being used as a sample analyzing apparatus for analyzing samples, such as biosubstances representative of functional substances, and a fluid handling unit for use therein.

2. Description of the Prior Art

As conventional methods for specifically detecting biosubstances, such as proteins, there are known various methods for causing an antigen-antibody reaction using an antibody to a specific biosubstance, to carry out the visual recognition or spectroscopic measurement of a reactant thus obtained, to detect the biosubstance.

As methods for quantifying a reactant obtained by an antigen-antibody reaction of a biosubstance, such as a protein, there are widely adopted some methods, such as ELISA (Enzyme-Linked ImmunoSorbent Assay). In these methods, there is used a sample analyzing apparatus called a microplate wherein a large number of fine recessed portions generally called microwells (which will be herein after referred to as "wells") are arrayed. The wall surfaces of the wells are coated with an antibody to a specific biosubstance, which is a target substance, as a capturing (or catching) material, to capture (or catch) the target substance by the capturing material to detect the target substance by measuring a reactant, which is obtained by an antigen-antibody reaction between the target substance and the antibody, by fluorescence, luminous reagents or the like.

In a typical method using a microplate, such as ELISA, a well is filled with a liquid, such as a specimen containing a target substance or an antibody reagent, as a reaction solution to cause a reaction. This reaction does not occur until the components in the liquid filled in the well are moved by molecular diffusion to reach the bottom and inner walls of the well. For that reason, if a microplate is allowed to stand, a theoretical reaction time depends on the diffusion time of the components in the liquid filled in the well. Since the molecules in the liquid move while colliding with the surrounding molecules, the speed of diffusion is very slow. If the target substance is a protein having a molecular weight of about 70,000, the speed of diffusion is about 0.5 to $1\times10^{-6}$ $cm^2$/sec in a dilute aqueous solution (room temperature). Therefore, in the liquid filled in the well, the target substance located apart from the bottom and inner walls of the well is hardly allowed to react in a practical measuring time. In addition, since it is effective to cause the bottom and wall surfaces in the well serving as a reacting portion to uniformly contact the reaction solution in order to improve the efficiency of reaction in a microplate, it is required to use a larger quantity of liquid than the quantity of liquid required for the reaction.

Thus, in the conventional method using the microplate, such as ELISA, the antigen-antibody reaction proceeds only on the wall surface of the well coated with the capturing antibody. Therefore, the liquid must be allowed to stand until the reaction occurs after the target substance, antibody and substrate contained in the liquid fed into the well are suspended, circulated and sink to reach the wall surface of the well, so that there is a problem in that the efficiency of reaction is bad. In addition, in a microplate which is subdivided into a large number of wells, the quantity of liquid fed into each of the wells is limited, so that there is a problem in that the sensitivity of measurement is deteriorated.

There is known a method using a porous material as a capturing material as a method for improving the efficiency of reaction and the sensitivity of measurement. However, it is required to provide an external power, such as a pump, in order to control the flowability of liquid, and it is difficult to continuously control the flowability of liquid since the porous material is easily clogged up. There is also known a method for fluidizing liquid by pressurization or suction as a method using a microchip having a fine space to fluidize liquid in the fine space. However, it is also required to provide an external power and a complicated device in this method. Moreover, there is known a method using a microchip having a fine space to fluidize liquid in the fine space by a valve structure. However, it is also required to provide power or energy for operating the valve in this method.

In order to improve the sensitivity of measurement and shorten the measuring time in ELISA or the like, there is proposed a microplate capable of increasing the surface area of a reaction surface (capturing surface) to enhance the sensitivity of measurement by forming fine irregularities on the bottom surface of each of wells serving as the reaction surface (see, e.g., Japanese Patent Laid-Open No. 9-159673). There is also proposed a microchip capable of increasing the surface area of a reaction surface to enhance the efficiency of reaction in a fine space by arranging a fine solid particle (bead) as a reaction solid phase in a microchannel of the microchip (see, e.g., Japanese Patent Laid-Open No. 2001-4628). Moreover, there is proposed a microplate capable of increasing the surface area of a reaction surface and saving the quantity of samples by forming a small-diameter recessed portion in the central portion of the bottom of each of wells. (see, e.g., Japanese Patent Laid-Open No. 9-101302).

However, in the microplate proposed in Japanese Patent Laid-Open No. 9-159673, there is a problem in that it is not possible to improve the efficiency of reaction although it is possible to improve the sensitivity of measurement. In addition, the microchip proposed in Japanese Patent Laid-Open No. 2001-4628 is not suitable for the measurement of a large number of specimens although it is possible to improve the efficiency of reaction since it is a microchip having a microchannel structure, not a microplate typically used in ELISA or the like. Moreover, in the microplate proposed in Japanese Patent Laid-Open No. 9-101302, it is not possible to sufficiently improve the efficiency of reaction and the sensitivity of measurement, although it is possible to increase the surface area of the reaction surface to some extent to improve the efficiency of reaction and the sensitivity of measurement.

SUMMARY OF THE INVENTION

It is therefore an object of the present invention to eliminate the aforementioned problems and to provide a fluid handling apparatus which is capable of improving the efficiency of reaction and the sensitivity of measurement with a simple structure and of shortening a reaction time and a measuring time, when the apparatus is used as a sample analyzing apparatus for measuring a large number of specimens, and a fluid handling unit for use therein.

In order to accomplish the aforementioned and other objects, according to one aspect of the present invention, a fluid handling apparatus comprise an apparatus body and a plurality of fluid handling subassemblies arranged on the apparatus body, each of the fluid handling subassemblies comprising: an injecting section for injecting a fluid; a fluidized section for receiving the fluid from the injecting section to allow the fluid to continuously flow downwards; a fluid housing chamber for receiving the fluid from the fluidized section; a wall portion formed so as to extend in substantially vertical directions between the fluid housing chamber and the fluidized section; an opening, formed in the wall portion, for allowing the fluid in the fluidized section to enter the fluid housing chamber; and a surface-area increasing means, arranged in the fluidized section, for increasing an area of a contact surface with the fluid in the fluidized section.

In this fluid handling apparatus, the level of the bottom end of the opening is preferably substantially equal to the level of the bottom of the fluidized section. The apparatus body preferably comprises a frame and a plurality of supporting members which are arranged on the frame so as to be substantially parallel to each other, each of the supporting members having a plurality of recessed portions which are arranged at regular intervals in a row, and each of the plurality of fluid handling subassemblies being mounted in a corresponding one of the recessed portions. The fluidized section is preferably arranged so as to surround the fluid housing chamber. Each of the plurality of recessed portions may comprise an upper cylindrical recessed portion, and a lower cylindrical recessed portion which is formed in a bottom of the upper cylindrical recessed portion and which has a smaller diameter than that of the upper cylindrical recessed portion, the fluidized section being formed between a cylindrical member, which is inserted into each of the plurality of recessed portions, and the upper cylindrical recessed portion, the fluid housing chamber being formed in the cylindrical member, and the injecting section being formed over the surface-area increasing means. In this case, an extended recessed portion for extending the upper cylindrical recessed portion in substantially horizontal directions so as to facilitate the injection of the fluid is preferably formed in each of the plurality of recessed portions.

In the above described fluid handling apparatus, the surface-area increasing means preferably comprises a large number of fine particles filled in the fluidized section, but the surface-area increasing means may be a single member arranged in the fluidized section. Alternatively, the surface-area increasing means may be a sheet-like member which is wound so as to surround the fluid housing chamber in the fluidized section, or the surface-area increasing means may be a string type member which is wound so as to surround the fluid housing chamber in the fluidized section. Moreover, the opening is preferably closed by a mesh member for allowing the fluid to pass therethrough.

According to another aspect of the present invention, a fluid handling unit comprises a supporting member and a plurality of fluid handling subassemblies which are arranged on the supporting member at regular intervals in a row, each of the fluid handling subassemblies comprising: an injecting section for injecting a fluid; a fluidized section for receiving the fluid from the injecting section to allow the fluid to continuously flow downwards; a fluid housing chamber, formed so as to be surrounded by the fluidized section, for receiving the fluid from the fluidized section; a wall portion formed so as to extend in substantially vertical directions between the fluid housing chamber and the fluidized section; an opening, formed in the wall portion, for allowing the fluid in the fluidized section to enter the fluid housing chamber; and a surface-area increasing means, arranged in the fluidized section, for increasing an area of a contact surface with the fluid in the fluidized section.

In this fluid handling unit, the level of the bottom end of the opening is preferably substantially equal to the level of the bottom of the fluidized section. The surface-area increasing means preferably comprises a large number of fine particles filled in the fluidized section, but the surface-area increasing means may be a single member arranged in the fluidized section. Alternatively, the surface-area increasing means may be a sheet-like member which is wound so as to surround the fluid housing chamber in the fluidized section, or the surface-area increasing means may be a string type member which is wound so as to surround the fluid housing chamber in the fluidized section. Moreover, the opening is preferably closed by a mesh member for allowing the fluid to pass therethrough.

According to the present invention, it is possible to provide a fluid handling apparatus which is capable of improving the efficiency of reaction and the sensitivity of measurement with a simple structure and of shortening a reaction time and a measuring time, when the apparatus is used as a sample analyzing apparatus for measuring a large number of specimens, and a fluid handling unit for use therein.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a fluid handling apparatus and a fluid handling unit for use therein according to the present invention will be described below in detail.

Figure 1:
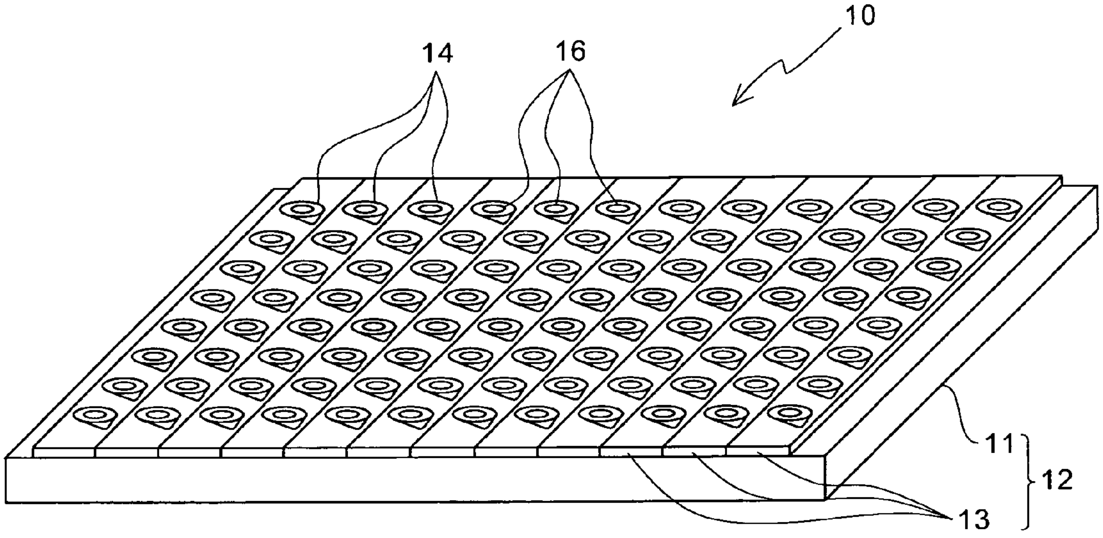
FIG. 1 is a perspective view of the preferred embodiment of a fluid handling apparatus according to the present invention.

FIGS. 1 through 7 show the preferred embodiment of a fluid handling apparatus according to the present invention. For example, the fluid handling apparatus 10 in this preferred embodiment can be used as an apparatus for analyzing a sample containing a biosubstance, such as a protein, which is representative of functional substances. In general, the fluid handling apparatus 10 can be used as a sample analyzing apparatus called a microwell plate for carrying out the measurement of a large number of specimens. As shown in FIG. 1, the fluid handling apparatus 10 comprises: an apparatus body 12; and a plurality of fluid handling subassemblies 16 (96(=8×12) fluid handling subassemblies in this preferred embodiment) mounted on the apparatus body 12.

Figure 2:
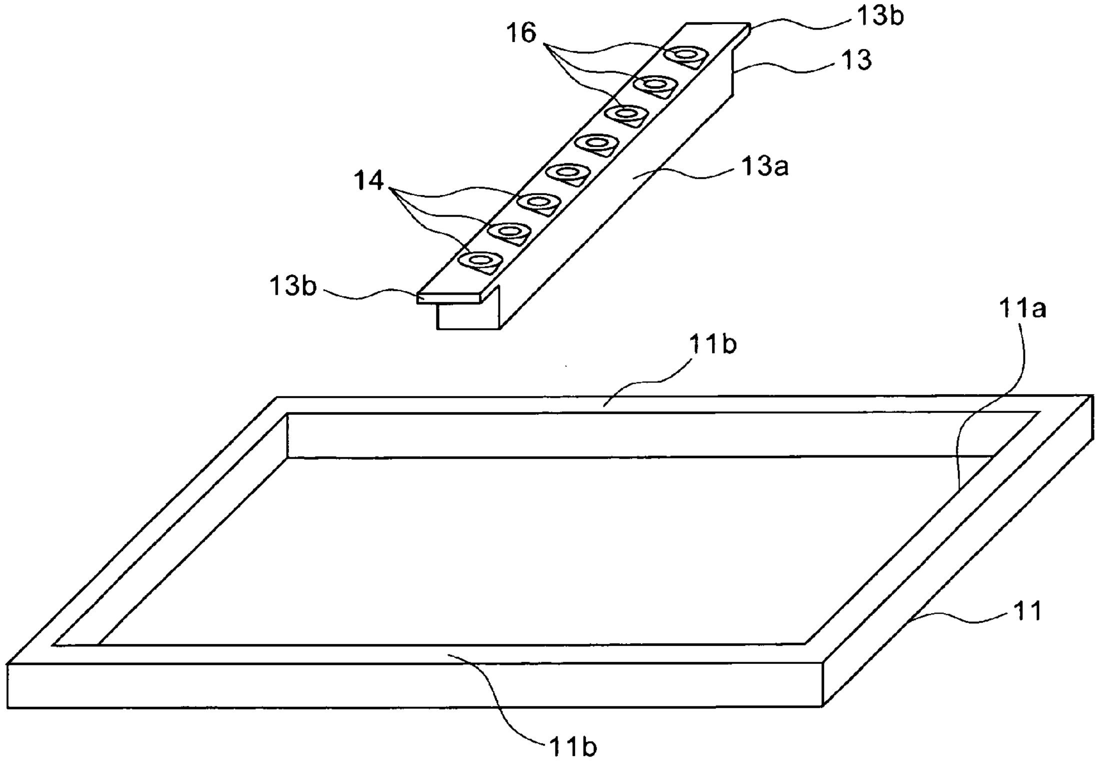
FIG. 2 is a perspective view showing a frame and a fluid handling subassemblies supporting member of the apparatus body of the fluid handling apparatus of FIG. 1.
Figure 3:
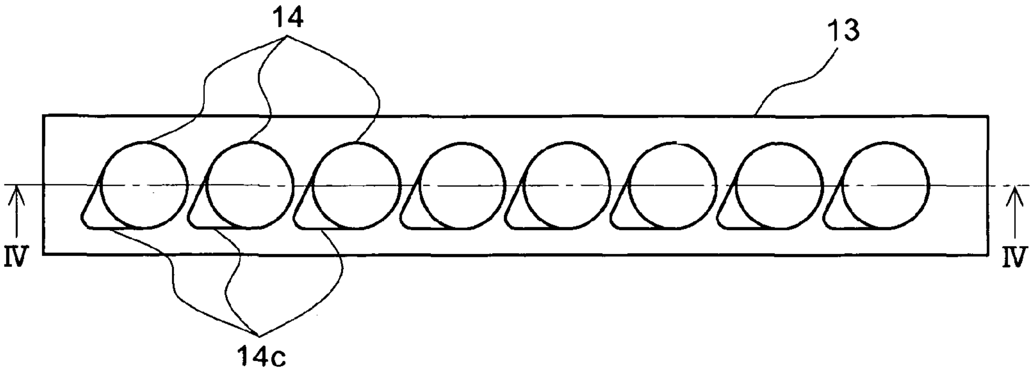
FIG. 3 is an enlarged plan view of the fluid handling subassemblies supporting member of FIG. 2.
Figure 4:
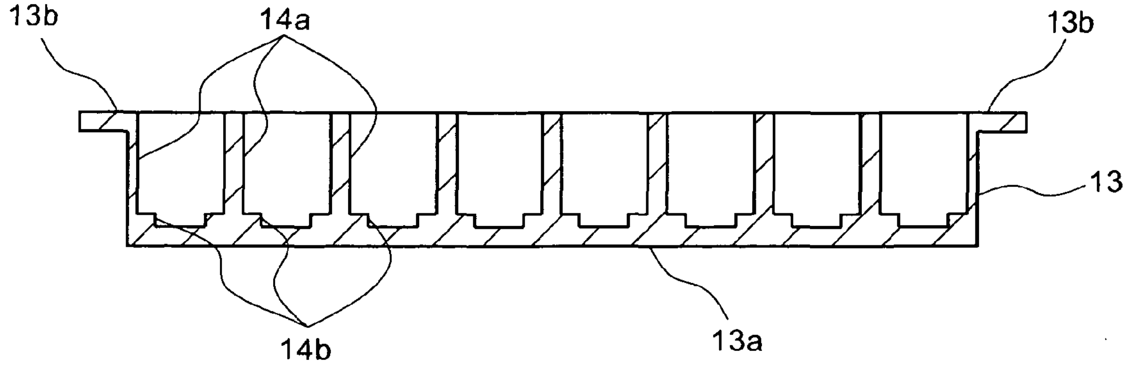
FIG. 4 is a sectional view taken along line IV-IV of FIG. 3.

As shown in FIGS. 1 and 2, the apparatus body 12 is made of a resin material, such as polycarbonate (PC) or polymethyl methacrylate (PMMA), or a glass material, and comprises: a substantially rectangular frame 11 which has a substantially rectangular opening 11*a* in the center thereof and which has a thickness of a few millimeters, the length of each side of the frame 11 being in the range of from a few centimeters to over ten centimeters; and a plurality of fluid handling subassemblies supporting members 13 (12 fluid handling subassemblies supporting members in this preferred embodiment) mounted on the frame 11. Furthermore, the opening 11*a* of the frame 11 may be a through hole or a recessed portion with bottom. Alternatively, the frame 11 may be a standard frame, such as a frame for microplate of SBS (Society for Biomolecular Screening) standard. The fluid handling subassemblies supporting members 13 may be made of a transparent material. However, if the fluid handling apparatus 10 in this preferred embodiment is used for measuring fluorescence, the fluid handling subassemblies supporting members 13 is preferably made of a member (e.g., a black member) which is difficult to allow light to pass through the member in order to suppress the rise of background during the measurement of fluorescence.

As shown in FIG. 2, each of the fluid handling subassemblies supporting members 13 comprises: an elongated supporting member body 13*a* having a shape of substantially rectangular parallelepiped, the length of which is substantially equal to the width of the opening 11*a* of the frame 11; and a pair of substantially rectangular protruding portions 13*b* which protrude from the upper portions of the supporting member body 13*a* at both ends in longitudinal directions to extend along the upper surface of the supporting member body 13*a*. As shown in FIG. 1, the supporting member bodies 13*a* of the fluid handling subassemblies supporting members 13 are inserted into the opening 11*a* of the frame 11 to be mounted on the frame 11 substantially in parallel and adjacent to each other so that the protruding portions 13*b* are supported on a pair of upper surfaces 11*b* of the frame 11 extending in longitudinal directions. Thus, the apparatus body 12 is assembled.

As shown in FIGS. 1 through 4, a plurality of recessed portions 14 (eighth recessed portions 14 in this preferred embodiment) (which will be hereinafter referred to as "mounting recessed portions 14") are formed in the upper surface of the supporting member body 13*a* of each of the fluid handling subassemblies supporting members 13 so as to be arranged at regular intervals in a row. In each of the mounting recessed portions 14, one of the fluid handling subassemblies 16 is mounted. Each of the mounting recessed portions 14 comprises: a substantially cylindrical large-diameter recessed portion 14*a* formed in the upper surface of the supporting member body 13*a*; an extended recessed portion 14*c* which is adjacent to the large-diameter recessed portion 14*a* to be formed in the upper surface of the supporting member body 13 so as to extend the upper portion of the large-diameter recessed portion 14*a* substantially in horizontal directions and which has a shape of substantially triangle pole having a half depth of the large-diameter recessed portion 14*a*; and a substantially cylindrical small-diameter recessed portion 14*b* which is formed in a substantially central portion of the bottom of the large-diameter recessed portion 14*a*. One of two surfaces of the extended recessed portion 14*c* extending from the large-diameter recessed portion 14*a* extends along the side of the supporting member body 13*a* of the fluid handling subassemblies supporting member 13 extending in longitudinal directions (see FIG. 5), and the bottom of the extended recessed portion 14*c* is inclined downwards as a distance from the large-diameter recessed portion 14*a* is decreased (see FIG. 6).

Figure 5:
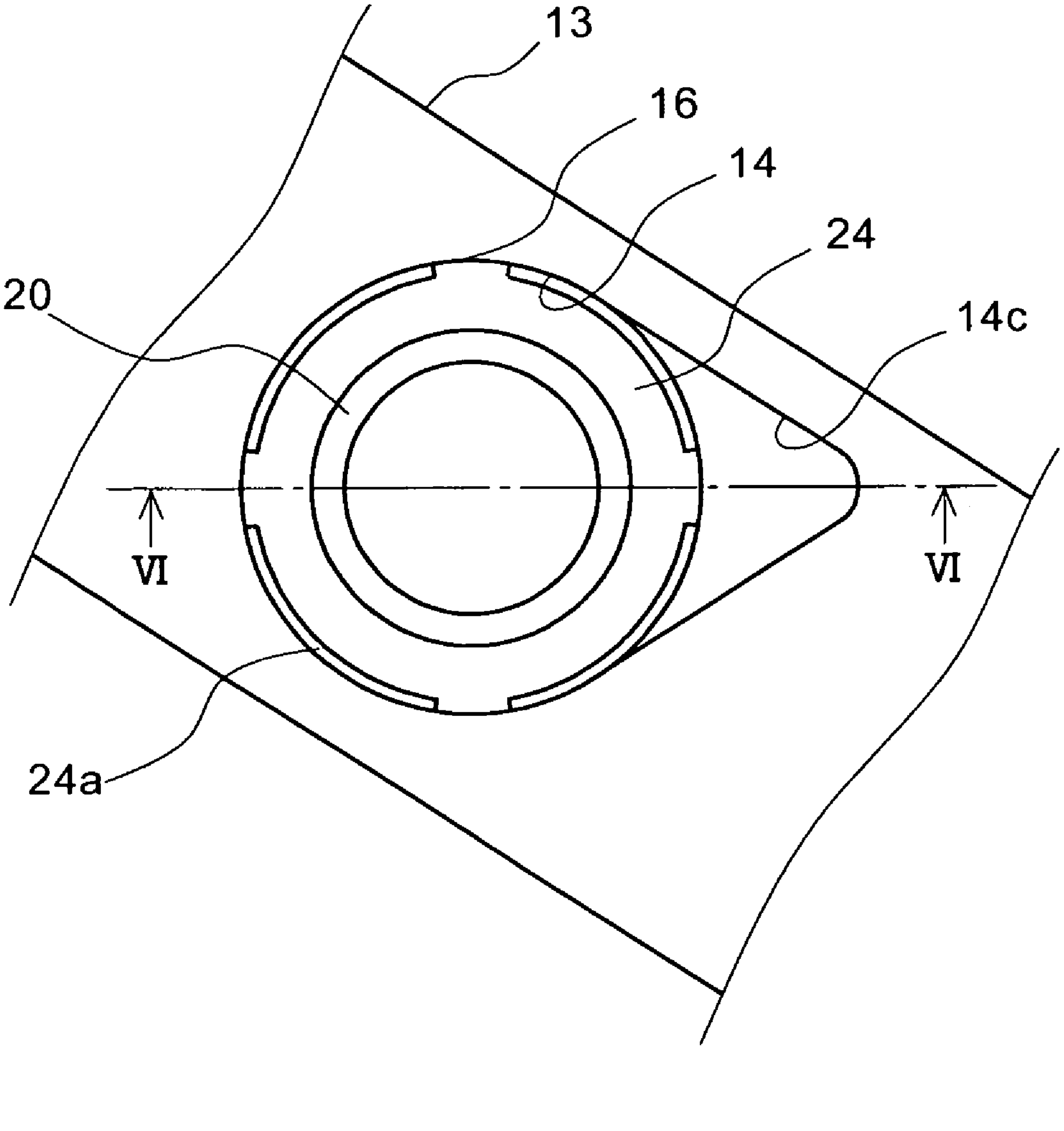
FIG. 5 is an enlarged plan view of one of the fluid handling subassemblies of the fluid handling apparatus of FIG. 1.
Figure 6:
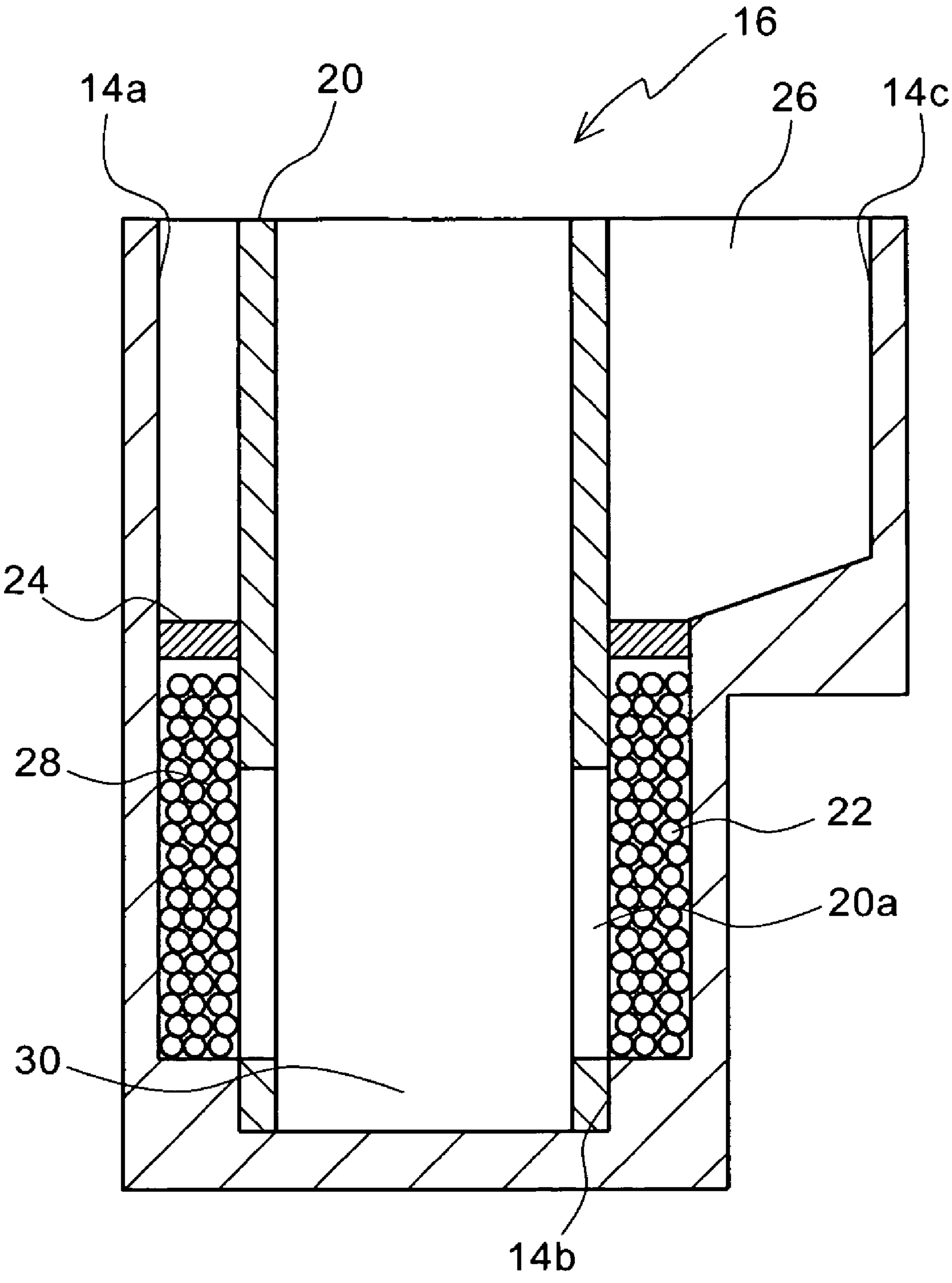
FIG. 6 is a sectional view taken along line VI-VI of FIG. 5.
Figure 7:
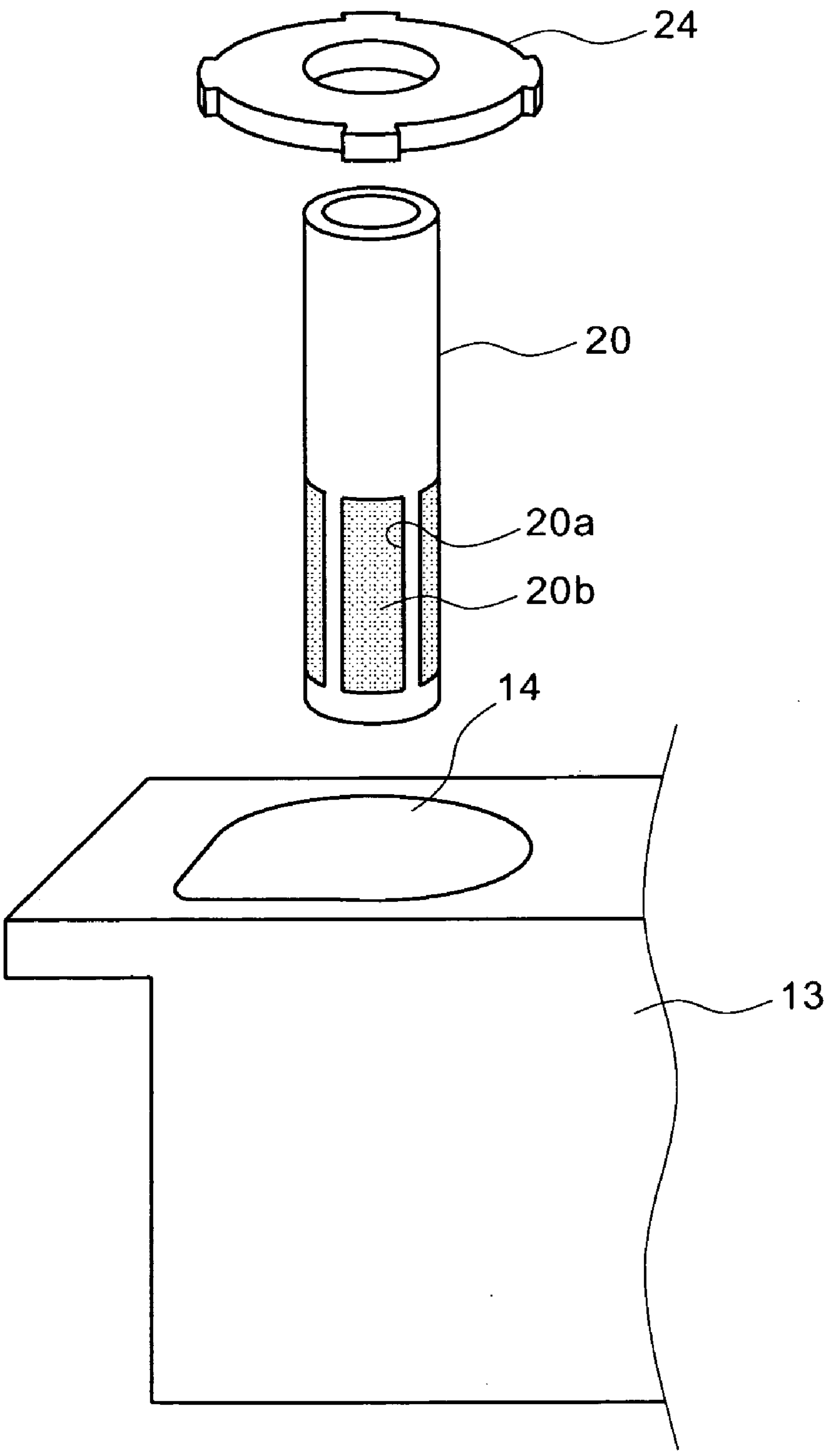
FIG. 7 is an exploded perspective view of one of the fluid handling subassemblies of the fluid handing apparatus of FIG. 1, except for beads.

FIGS. 5 through 7 are enlarged views showing one of the fluid handling subassemblies 16, each of which is mounted in a corresponding one of the mounting recessed portions 14 of the fluid handling apparatus 10 in this preferred embodiment. FIG. 5 is a plan view of one of the fluid handling subassemblies 16, each of which is mounted in a corresponding one of the mounting recessed portions 14 of the fluid handling apparatus 10. FIG. 6 is a sectional view taken along line VI-VI of FIG. 5. FIG. 7 is an exploded perspective view of one of the fluid handling subassemblies 16 (except for beads 22).

As shown in FIGS. 5 through 7, each of the fluid handling subassemblies 16 comprises: a cylindrical member 20 having a substantially cylindrical shape which has a diameter and height of a few millimeters; a large number of substantially spherical fine beads 22; and a substantially annular disk-shaped lid member 24.

As shown in FIG. 6, the cylindrical member 20 has a length which is substantially equal to the depth of the mounting recessed portion 14 (the depth of the large-diameter recessed portion 14*a* and small-diameter recessed portion 14*b*), and an outside diameter which is substantially equal to the inside diameter of the small-diameter recessed portion 14*b* of the mounting recessed portion 14. The bottom portion of the cylindrical member 20 is designed to be fitted into the small-diameter recessed portion 14*b* of the mounting recessed portion 14. Furthermore, since the extended portion 14*c* is formed in this preferred embodiment, even if the outside diameter of the cylindrical member 20 is increased to decrease a gap between the cylindrical member 20 and the large-diameter recessed portion 14*a*, it is possible to ensure a sufficiently large inlet of an injecting section 26 which will be described later. For example, the inside diameter of the cylindrical member 20 can be about 4.5 mm. The outer periphery of the cylindrical member 20 has one or a plurality of openings 20*a* (four openings 20*a* in this preferred embodiment, and only two openings 20*a* are shown in FIG. 6) which pass through the cylindrical member 20 so as to extend in longitudinal directions. The length of each of the openings 20*a* is less than half of the length of the cylindrical member 20, and the level of the bottom end of each of the openings 20*a* is substantially equal to the level of the bottom of the large-diameter recessed portion 14*a* when the bottom portion of the cylindrical member 20 is fitted into the small-diameter recessed portion 14*b* of the mounting recessed portion 14. The openings 20*a* are closed by a mesh member 20*b* which allows fluid to pass there through and which prevents beads 22 from passing therethrough. If the openings 20*a* are thus closed by the mesh member 20*b*, it is possible to use small beads, and it is possible to sufficiently ensure the flow rate of fluid passing through the openings 20*a*.

The central portion of the lid member 24 has a substantially circular opening into which the cylindrical member 20 is fitted. The peripheral portion of the lid member 24 has a plurality of cut-out portions 24*a* (four cut-out portions 24*a* in this preferred embodiment) serving as inlets which extend in circumferential directions at regular intervals. The outside diameter of the lid member 24 is substantially equal to the inside diameter of the large-diameter recessed portion 14*a* of the mounting recessed portion 14, so that the lid member 24 is fitted into the mounting recessed portion 14 when it is inserted into the mounting recessed portion 14.

In order to assemble the fluid handling subassembly 16 with this construction, the lower portion of the cylindrical member 20 is first fitted into the small-diameter recessed portion 14*b* of the mounting recessed portion 14, and the lower end thereof is fixed to the bottom surface of the small-diameter recessed portion 14*b* of the mounting recessed portion 14 with an adhesive or the like. Then, a large number of beads 22 are filled in an annular space between the large-diameter recessed portion 14*a* of the mounting recessed portion 14 and the cylindrical member 20. Then, the cylindrical member 20 is fitted into the opening of the lid member 24 which is arranged on the beads 22 to be fixed to the mounting recessed portion 14 and cylindrical member 20 with an adhesive or the like.

If the fluid handling subassembly 16 is thus mounted in the mounting recessed portion 14, a space serving as an injecting section 26 for injecting a fluid, such as a liquid sample, is formed between the cylindrical member 20 and the large-diameter recessed portion 14*a* and extended recessed portion 14*c* of the mounting recessed portion 14 over the lid member 124. Below the injecting section 26, a fluidized section 28, which is a substantially annular space capable of being used as a reaction section filled with the large number of beads 22, is formed between the large-diameter recessed portion 14*a* of the mounting recessed portion 14 and the cylindrical member 20. The fluidized section 28 is communicated with the injecting section 26 via the cut-out portions 24*a* of the lid member 24 serving as inlets. In the cylindrical member 20, there is formed a fluid housing chamber 30 which is a substantially cylindrical space capable of being used as a measuring section.

If a fluid is injected into the fluidized section 28 from the cut-out portions 24*a* of the lid member 24 serving as the inlets, the fluid flows downwards in the fluidized section 28 filled with the large number of beads 22, and then, passes through the openings 20*a* of the cylindrical member 20 to be fed into the interior of the cylindrical member 20 (the fluid housing chamber 30).

If the fluidized section 28 is thus filled with the large number of beads 22, it is possible to increase the surface area of the inner surface of the passage in the fluidized section 28. Thus, when the fluid handling apparatus 10 is used as a sample analyzing apparatus, if the surface of the beads 22 is utilized as a supporting surface (a reaction surface) for a capturing material, it is possible to increase the surface area of the supporting surface (the reaction surface) for the capturing material to increase the contact area with the fluid. If a liquid is allowed to continuously flow on the large reaction surface, it is possible to enhance the efficiency of reaction, and it is possible to shorten the reaction time and improve the sensitivity of measurement.

In this preferred embodiment, if the fluid handling subassemblies 16 are mounted on each of the fluid handling subassemblies supporting members 13 of the apparatus body 12, a fluid handling unit, on which the plurality of fluid handling subassemblies 16 are arranged at regular intervals in a row, can be mounted on the frame 11 of the apparatus body 12. Since the fluid handling unit can be thus mounted on the frame 11 every row, it is possible to easily handle the fluid handling apparatus 10.

In this preferred embodiment, since the openings 20*a* of the cylindrical member 20 are closed by the mesh member 20*b*, it is possible to hold sufficiently fine beads 22 in the fluidized section 28 even if the size of the openings 20*a* of the cylindrical member 20 is increased. Therefore, it is possible to further improve the efficiency of reaction, and it is possible to increase the flow rate of the fluid passing through the openings 20*a* by increasing the size of the openings 20*a* of the cylindrical member 20. However, if it is possible to hold sufficiently fine beads 22 in the fluidized section 28 and if it is possible to increase the flow rate of the fluid passing through the openings 20*a*, the openings 20*a* may be formed by a large number of slits, which are thinner than the diameter of the beads 22, without providing the mesh member 20*b*.

Figure 8:
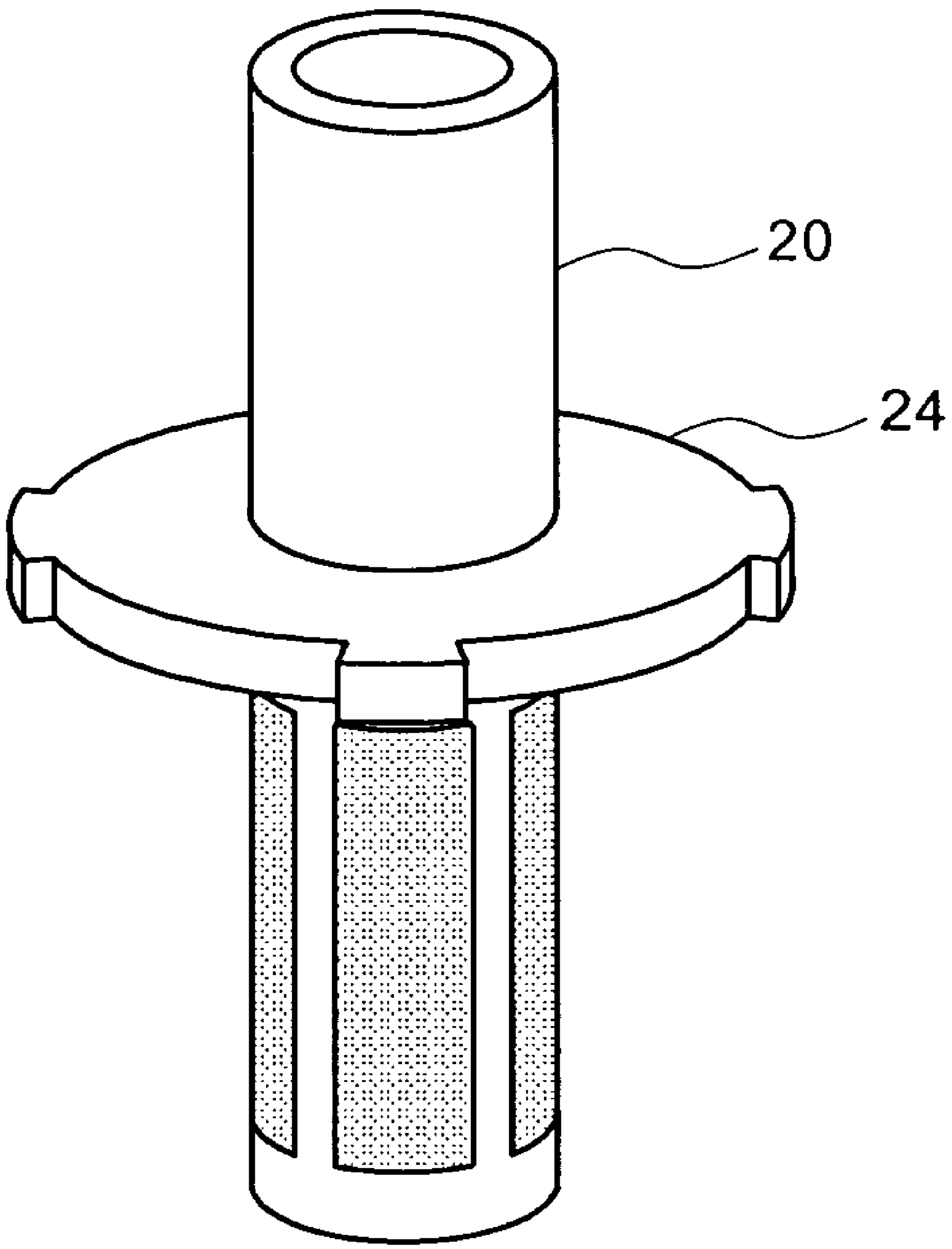
FIG. 8 is a perspective view showing a modified example of a cylindrical member of the fluid handling apparatus of FIG. 7.

While the cylindrical member 20 has been fitted into the opening of the lid member 24 in the above described preferred embodiment, the cylindrical member 20 may be integrally formed with the lid member 24 as shown in FIG. 8. In addition, the surface of the mounting recessed portion 14 is preferably caused to have a hydrophilic property. Moreover, the peripheral portion of the bottom of the large-diameter recessed portion 14*a* of the mounting recessed portion 14 serving as the bottom of the fluidized section 28 (the corner portion between the bottom and peripheral surfaces of the large-diameter recessed portion 14*a*) is preferably chamfered as R shape so that the interior of the fluidized section 28 can be easily washed.

Figure 9:
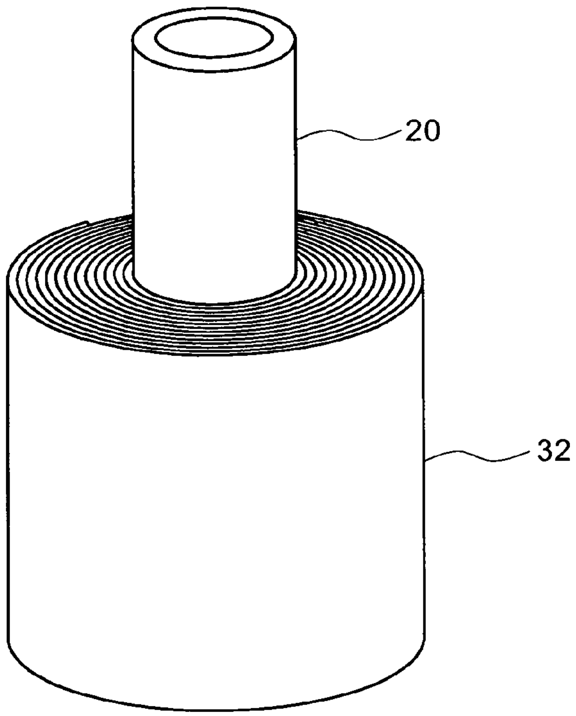
FIG. 9 is a perspective view showing a state that a sheet-like member is wound onto a cylindrical member in place of beads as a modified example of one of the fluid handling subassemblies of the preferred embodiment of a fluid handling apparatus according to the present invention.
Figure 10:
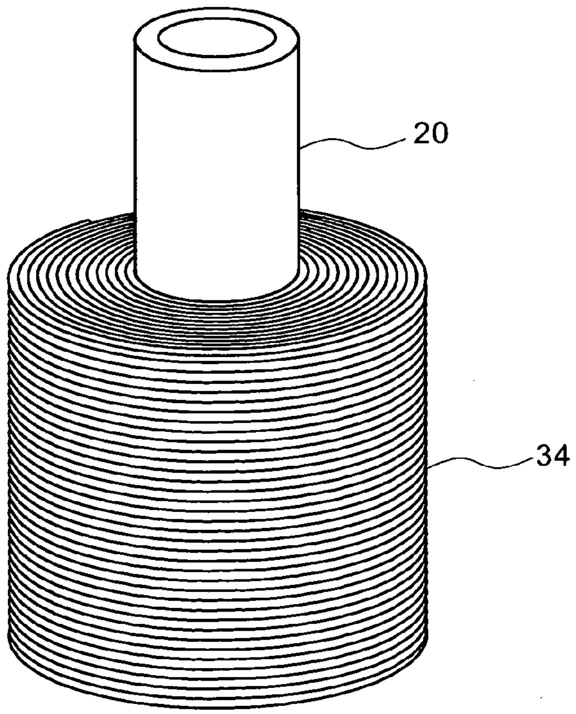
FIG. 10 is a perspective view showing a state that a string type member is wound onto a cylindrical member in place of beads as a modified example of one of the fluid handling subassemblies of the preferred embodiment of a fluid handling apparatus according to the present invention.

In place of the beads 22, a single member for allowing the high flowability of the fluid, such as a monolithic porous member capable of being housed in the fluidized section 28, may be housed in the fluidized section 28. Alternatively, a sheet-like member 32 having a mesh structure, fiber structure, porous structure or the like may be wound onto the lower portion of the cylindrical member 20 as shown in FIG. 9, or a string type member 34 may be wound onto the lower portion of the cylindrical member 20 as shown in FIG. 10. Moreover, the beads 22, the sheet-like member shown in FIG. 9 or the string type member shown in FIG. 10 may be formed as a monolithic member, which can be housed in the fluidized section 28, to be housed in the fluidized section 28.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A fluid handling apparatus comprising an apparatus body and a plurality of fluid handling subassemblies arranged on the apparatus body, each of the fluid handling subassemblies comprising:

an injecting section for injecting a fluid;

a fluidized section, formed below the injecting section, for receiving the fluid from the injecting section to allow the fluid to continuously flow downwards;

a fluid housing chamber, formed so as to be surrounded by the fluidized section, for receiving the fluid from the fluidized section;

a wall portion formed so as to extend in substantially vertical directions between the fluid housing chamber and the fluidized section;

an opening, formed in the wall portion so as to extend in substantially vertical directions, for allowing the fluid in the fluidized section to enter the fluid housing chamber, the level of the bottom end of the opening is substantially equal to the level of the bottom of the fluidized section; and a surface-area increasing means, arranged in the fluidized section, for increasing an area of a contact surface with the fluid in the fluidized section.

2. A fluid handling apparatus as set forth in claim 1, wherein said apparatus body comprises a frame and a plurality of supporting members which are arranged on the frame so as to be substantially parallel to each other, each of the supporting members having a plurality of recessed portions which are arranged at regular intervals in a row, and each of said plurality of fluid handling subassemblies being mounted in a corresponding one of the recessed portions.

3. A fluid handling apparatus as set forth in claim 2, wherein each of said plurality of recessed portions comprises an upper cylindrical recessed portion, and a lower cylindrical recessed portion which is formed in a bottom of said upper cylindrical recessed portion and which has a smaller diameter than that of said upper cylindrical recessed portion, said fluidized section being formed between a cylindrical member, which is inserted into each of said plurality of recessed portions, and said upper cylindrical recessed portion, said fluid housing chamber being formed in said cylindrical member, and said injecting section being formed over said surface-area increasing means.

4. A fluid handling apparatus as set forth in claim 3, wherein an extended recessed portion for extending said upper cylindrical recessed portion in substantially horizontal directions so as to facilitate the injection of said fluid is formed in each of said plurality of recessed portions.

5. A fluid handling apparatus as set forth in claim 1, wherein said surface-area increasing means comprises a large number of fine particles filled in said fluidized section.

6. A fluid handling apparatus as set forth in claim 1, wherein said surface-area increasing means is a single member arranged in said fluidized section.

7. A fluid handling apparatus as set forth in claim 1, wherein said surface-area increasing means is a sheet-like member which is wound so as to surround said fluid housing chamber in said fluidized section.

8. A fluid handling apparatus as set forth in claim 1, wherein said surface-area increasing means is a string type member which is wound so as to surround said fluid housing chamber in said fluidized section.

9. A fluid handling apparatus as set forth in claim 1, wherein said opening is closed by a mesh member for allowing said fluid to pass therethrough.

10. A fluid handling unit comprising a supporting member and a plurality of fluid handling subassemblies which are arranged on the supporting member at regular intervals in a row, each of said fluid handling subassemblies comprising:

an injecting section for injecting a fluid;

a fluidized section, formed below the injecting section, for receiving the fluid from the injecting section to allow the fluid to continuously flow downwards;

a fluid housing chamber, formed so as to be surrounded by the fluidized section, for receiving the fluid from the fluidized section;

a wall portion formed so as to extend in substantially vertical directions between the fluid housing chamber and the fluidized section;

an opening, formed in the wall portion so as to extend in substantially vertical directions, for allowing the fluid in the fluidized section to enter the fluid housing chamber, the level of the bottom end of the opening is substantially equal to the level of the bottom of the fluidized section; and a surface-area increasing means, arranged in the fluidized section, for increasing an area of a contact surface with the fluid in the fluidized section.

11. A fluid handling unit as set forth in claim 10, wherein said surface-area increasing means comprises a large number of fine particles filled in said fluidized section.

12. A fluid handling unit as set forth in claim 10, wherein said surface-area increasing means is a single member arranged in said fluidized section.

13. A fluid handling unit as set forth in claim 10, wherein said surface-area increasing means is a sheet-like member which is wound so as to surround said fluid housing chamber in said fluidized section.

14. A fluid handling unit as set forth in claim 10, wherein said surface-area increasing means is a string type member which is wound so as to surround said fluid housing chamber in said fluidized section.

15. A fluid handling unit as set forth in claim 10, wherein said opening is closed by a mesh member for allowing said fluid to pass therethrough.

* * * * *